United States Patent [19]

Asselineau et al.

[11] Patent Number: 5,288,370

[45] Date of Patent: Feb. 22, 1994

[54] PROCESS FOR THE SEPARATION OF BUTENES AND BUTANES BY EXTRACTIVE DISTILLATION

[75] Inventors: Lionel Asselineau, Paris; Alexandre Rojey, Rueil Malmaison, both of France

[73] Assignee: Institut Francais Du Petrole, Rueil Malmaison, France

[21] Appl. No.: 855,755

[22] Filed: Mar. 20, 1992

[30] Foreign Application Priority Data

Mar. 20, 1991 [FR] France .............. 91/03 477

[51] Int. Cl.$^5$ .............................................. B01D 3/40
[52] U.S. Cl. ...................................... 203/51; 203/52; 203/56; 203/58; 203/60; 203/63; 203/68; 203/69; 203/78; 203/80; 585/802; 585/809; 585/860; 585/865; 585/866; 585/867
[58] Field of Search .................... 203/58, 51, 73, 56, 203/80, 78, 52, 63, 68, 69, 60; 585/860, 802, 809, 810, 865, 866, 867

[56] References Cited

U.S. PATENT DOCUMENTS

| | | | |
|---|---|---|---|
| 3,898,135 | 8/1975 | Tidwell et al. | 203/60 |
| 4,081,332 | 3/1978 | Hein | 203/60 |
| 4,134,795 | 1/1979 | Howat, III | 203/60 |
| 4,379,025 | 4/1983 | Yudovich et al. | 203/40 |
| 4,419,188 | 12/1983 | McCall | 203/24 |
| 4,515,661 | 5/1985 | Ogura et al. | 203/60 |
| 4,555,312 | 11/1985 | Ogura | 203/60 |
| 4,556,461 | 12/1985 | Ogura et al. | 203/60 |
| 4,629,533 | 12/1986 | Drake | 203/51 |
| 5,100,515 | 3/1992 | Lee et al. | 203/58 |

FOREIGN PATENT DOCUMENTS

| | | | |
|---|---|---|---|
| 1186461 | 2/1965 | Fed. Rep. of Germany | 260/669 R |
| 0667537 | 6/1979 | U.S.S.R. | 203/58 |

*Primary Examiner*—Virginia Manoharan
*Attorney, Agent, or Firm*—Millen, White, Zelano & Branigan

[57] ABSTRACT

For the separation of butenes and butanes by extractive distillation, a charge mainly containing butenes and butanes is contacted in an extractive distillation column under pressure with a first selective polar solvent, S1 (e.g., dimethyl formamide), the butanes being collected at the top. The solvent S1 containing the butenes and passing out at the bottom is mixed with a second solvent, S2, having a boiling point intermediate between that of butenes and that of the solvent S1, the mixture passing into a desorption column under pressure, where the butenes are collected at the top. The mixture of solvent S1 and S2 is separated in a purification column under atmospheric pressure, the solvent S2 passing out at the top is recycled to the desorption column, and the solvent S1 passing out at the bottom is recycled to the extractive distillation column.

22 Claims, 1 Drawing Sheet

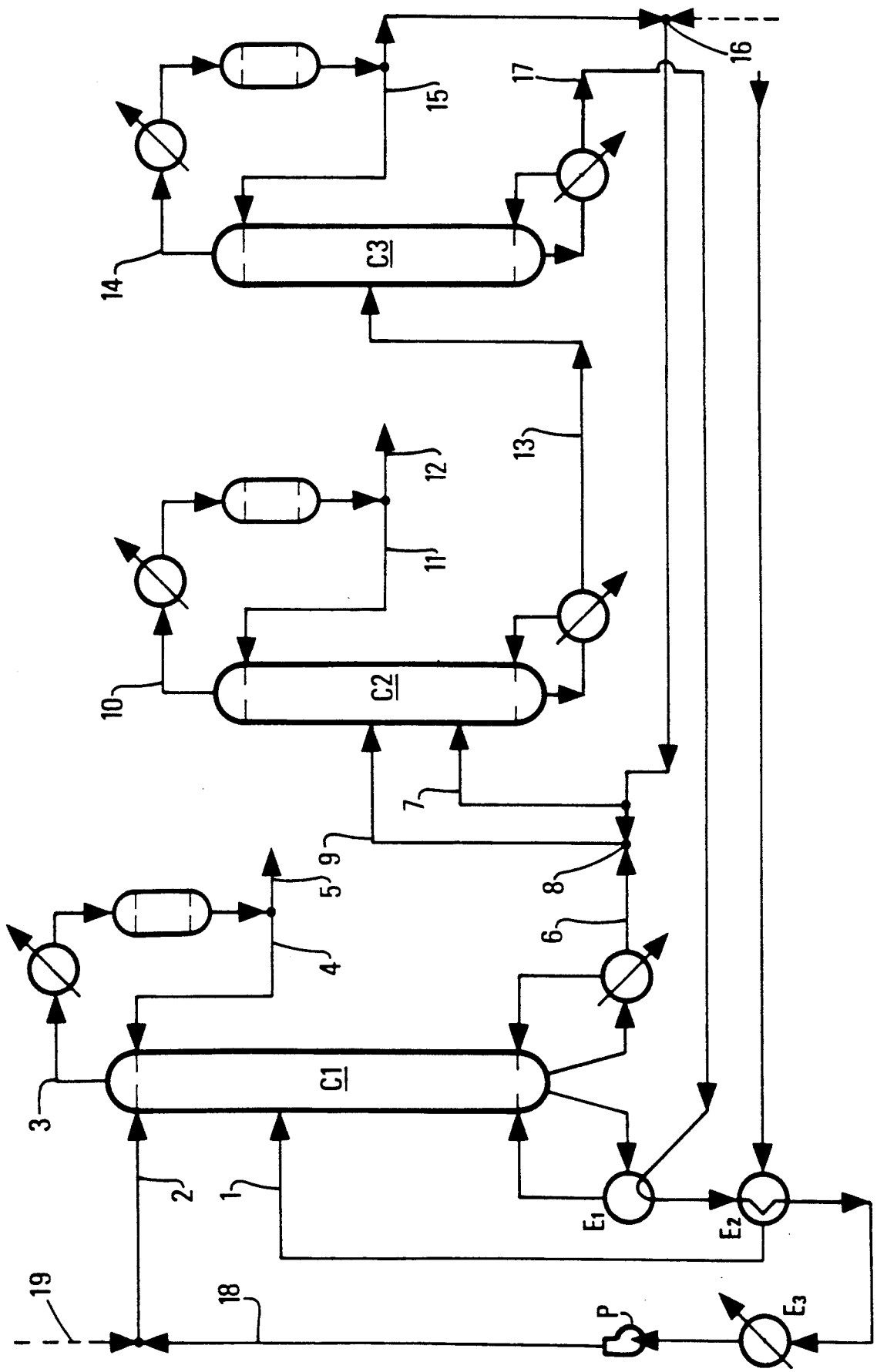

PROCESS FOR THE SEPARATION OF BUTENES AND BUTANES BY EXTRACTIVE DISTILLATION

BACKGROUND OF THE INVENTION

The invention relates to a process for the separation of butanes and butenes by extractive distillation.

In the treatment of the $C_4$ fraction resulting from steam cracking or catalytic cracking, the separation of butanes and butenes generally takes place downstream of the stages for the extractive distillation of 1,3-butandiene and the synthesis unit of methyl tert. butyl ether (MTBE). Thus, a $C_4$ fraction is obtained, which is free from 1,3-butadiene and highly depleted in isobutene.

As butenes are valuable products, they are separated from butanes. Thus, the butenes can be separated into 1-butene and 2-butenes, or isomerized into isobutene, which is recycled in the MTBE synthesis unit. Butenes can also be dimerized by the DIMERSOL (registered trademark) process into products usable in gasoline. This dimerization is a process performed by homogeneous catalysis in which the catalyst is consumed. As the efficiency of the catalyst is proportional to its concentration in the charge, a paraffin-free charge leads to catalyst economies. Moreover, the butenes which have not reacted can be recycled if the butanes are previously removed from the charge.

It is known to separate butanes and butenes in a $C_4$ fraction by extractive distillation. A prior art process (S. OGURA, T. ONDA, Advances in $C_4$ Hydrocarbon Processing AIChE 1987 Summer National Meeting, Aug. 16-19, 1987) consists of carrying out extractive distillation with as the solvent dimethyl formamide (DMF) under pressure, solvent recovery taking place under atmospheric pressure and the purification of the butenes takes place under pressure. The extractive distillation column bottom product is fed into a column under atmospheric pressure, in which the butenes are desorbed and pass out at the top with part of the solvent, while the bottom product is constituted by virtually pure DMF. The top butenes are then passed to a column under pressure for purification. The solvent recovered at the bottom of the latter column and which still contains butenes is returned to the atmospheric column.

The disadvantage of operating according to this process is that most butenes in the charge must be distilled twice which, bearing in mind the necessary recompression of the butene vapours, leads to a high energy consumption.

In an earlier-dated application filed by the present applicant on 26.2.1991 under French national registration No. 91/02385, a description is given of a process for the separation of butenes and butanes, in which the charge containing the butanes and butenes to be separated is introduced into an extractive distillation column under pressure, where it is contacted with a polar solvent in which the butanes have a higher volatility than the butenes, the distillate passing out at the top consisting essentially of separated butanes. The residue collected at the bottom and mainly consisting of the solvent and the butenes, is passed into a column under pressure, where the bottom temperature is adjusted in such a way that the desorption of the butenes is not complete, which makes it possible to limit the column bottom temperature and consequently avoid the thermal decomposition of the solvent.

The solvent which passes out at the bottom and which contains a fraction of the butenes is passed into a purification column under a pressure close to atmospheric pressure and whose operation is regulated in such a way that the overhead vapor, mainly constituted by butenes, also contains a fraction of the solvent, which makes it possible to partly condense it in order to ensure the reflux of the column, while avoiding compression at this stage. The vapor distillate is passed, after compression, into the desorption column under pressure. The purified solvent passing out at the bottom is recycled to the extractive distillation column.

SUMMARY OF THE INVENTION

It has not been discovered that it is possible to modify this process by making a second, appropriately chosen solvent fulfil the function of the fraction of the butenes which was kept mixed with the polar solvent in the residue of the desorption column (i.e., lower the boiling point of said residue so as to avoid any thermal deterioration of the solvent). The use of a second solvent makes it possible to obviate the compression stage of the vapor effluent of the purification column which, constituted mainly by butenes, had to be recycled to the desorption column under pressure. Thus, the process according to the invention can be more simply performed.

The separation process for butenes and butanes according to the present invention is generally defined in the same way as the process of the earlier-dated application, with certain modifications relating to the use of a secondary solvent.

As in the earlier-dated application, the charge to be treated is generally a $C_4$ steam of catalytic cracking fraction, from which the 1,3-butadiene has been removed, e.g., by extractive distillation and whose isobutene content may have been reduced, e.g., in a MTBE synthesis unit.

The charges considered here mainly consist of butenes (1-butene, cis 2-butene and trans 2-butene), n-butane, isobutane and isobutene in a small proportion and in the form of traces hydrocarbons with 3 to 5 carbon atoms.

A more particular composition of the charge can, e.g., be:

| | |
|---|---|
| isobutane: | 15 to 20% by weight |
| n-butane: | 7 to 15% by weight |
| 1-butene: | 20 to 25% by weight |
| isobutene: | <5% by weight |
| trans 2-butene: | 25 to 30% by weight |
| cis 2-butene: | 15 to 20% by weight. |

The solvent used as the first solvent in the process of the present invention and designated S1 can, as in the earlier-dated application, be any selective polar solvent, i.e., in which the butanes have a higher volatility than the butenes. As non-limitative examples reference can be made to monomethyl formamide (b.p.=182° C.), dimethyl formamide (b.p.=153° C.), diethyl formamide (b.p.=177.5° C.), dimethyl acetamide (b.p.=165° C.) and N-methyl pyrrolidone (b.p.=202° C.). Most frequently dimethyl formamide is used.

The second solvent referred to as S2 in the process according to the invention can be any organic compound condensable under atmospheric pressure and having a volatility intermediate between that of the first solvent and that of the butenes, which does not form an azeotrope with the butenes and which is miscible with the first solvent. It must be sufficiently volatile for the boiling point of the mixture which it forms at the bottom of the desorption column with the first solvent is sufficiently lowered, but must not be too volatile, so that its condensation on leaving the purification column remains relatively easy. A boiling point in the range 30° to 80° C. would appear to be appropriate for achieving the objectives of the invention. As non-limitative examples, reference can be made to hexane (b.p.=68° C.), cyclohexane (b.p.=80° C.), benzene (b.p.=80° C.), methyl tert. butyl ether (b.p.=55° C.), mixtures of these solvents and $C_5$ or $C_6$ hydrocarbon fractions (b.p. between 30° C. and 70° C.).

BRIEF DESCRIPTION OF THE DRAWING

The process according to the invention is described in greater detail hereinafter relative to the attached drawing, which is a single FIGURE exhibiting a simplified schematic flowsheet performance arrangement.

DETAILED DESCRIPTION OF THE FIGURE

In the figure charge to be treated and which has previously been heated e.g. to a temperature of 50° C. to 70° C. through the exchanger $E_2$, is introduced by the line 1 into the extractive distillation column C1 under a pressure p1 of 4 to 10 bars.

The extraction solvent, at a temperature below its boiling point at the considered pressure, is introduced by the line 2 into the upper part of the column C1. The solvent introduction temperature is, e.g., 50° to 90° C. The solvent flow rate can be in a weight ratio of 3 to 15 kg/kg with the charge flow rate. The column C1, e.g., operates at a bottom temperature of 90° to 140° C., with the top temperature at 30° to 70° C.

The distillate passing out at the top by line 3 mainly consists of isobutane and n-butane and possibly a little 1-butene and isobutene, as a function of the column setting. After condensation, a fraction of the distillate is passed as liquid reflux to the column C1 by the line 4. The remainder of the effluent is collected by the line 5, which can, e.g., be returned to the pool C4.

The residue passing out of the bottom of the column C1 through the line 6 and which essentially no longer contains butanes is passed into the desorption column C2 operating at a pressure p2 close to the pressure p1. Into the column C2 is also introduced by the line 7 a secondary solvent flow S2, in a quantity such that it is possible to collect butenes at the top of the column C2 at a temperature of 40° to 60° C. and at pressure p2, whilst maintaining the bottom temperature of, e.g., 150° to 170° C. below the temperatures at which the solvent S1 starts to significantly deteriorate. The quantity of solvent S2 is, e.g., 15 to 50% by weight of that of S1. The solvent S2 can optionally be mixed in 8 with the residue of column C1, the mixture then being introduced into the column C2 by the line 9.

The distillate passing out by the line 10 and constituted by separated butenes having a purity of, e.g., at least 97% by weight is condensed and returned in part, as reflux, by the line 11 to the column C2, the remainder being collected by the line 12. The residue of the column C2, passing out through the line 13 and consisting mainly of a mixture of solvents S1 and S2 is passed into the purification column C3 working at a pressure p3 of approximately 1 bar, e.g., 1 to 3 bars, and at a bottom temperature of 140° to 170° C. and a top temperature of 40° to 60° C.

The distillate passing out of the top of the column C3 by the line 14 essentially consists of the solvent S2 and can contain a small proportion of solvent S1. It is condensed and partly returned as reflux to the column C3 by the line 15. The other part, following a possible topping up at 16, is supplied to the column C2 by the line 7, or is remixed at 8 with the bottom of the extractive distillation column C1, in order to form the mixture supplying the desorption column C2 through line 9.

The bottom residue of the column C3, passing out through the line 17, is substantially pure solvent S1. It is recycled to the extractive distillation column C1. The thermal energy carried by this solvent S1, generally at a temperature of 150° to 170° C., can be partly used for heating the bottom of the column C1 via the exchanger E1 and partly for reheating the charge to its bubble point via the exchanger E2. The flow of solvent S1 can also be cooled through the exchanger E3 before being supplied by the pump P and the line 18 to the column C1. A top up of solvent can be carried out by the line 19.

The process according to the invention leads to butenes with a degree of purity of, e.g., approximately 97% by weight or higher, if necessary, mainly as a function of the proportion of solvent S1 used and the efficiency (number of trays) of the extractive distillation column.

In the present description, the indicated pressures are absolute pressures and 1 bar equals 0.1 MPa.

A practical example of the inventive process is given below.

EXAMPLE

The charge to be treated is a hydrocarbon mixture, whose composition is given in the second column of the table. The solvent S1 used is dimethyl formamide (DMF) and the solvent S2 is hexane.

The columns used have the following characteristics. The extractive distillation column C1 is a diameter 50 mm steel column with 100 perforated overflow trays. The desorption column C2 is a diameter 50 mm steel column having 65 perforated overflow trays. The purification column C3 is a diameter 50 mm glass column with 20 trays.

Each of these columns is made adiabatic, by thermal compensation for the steel columns and by thermal insulation for the glass column.

Column C1 is supplied at the 62nd tray (the trays are counted from top to bottom) by 435 g/h of charge and a temperature of 52° C. At the level of the 10th tray, it is supplied by the solvent, i.e. dimethyl formamide, at a temperature of 65° C. and a flow rate of 2770 g/h. The pressure is 5.6 bars, the reflux ratio 7.25 and the column is regulated to supply 129 g/h of distillate. The composition of the distillate produced is given in the third column of the table.

Column C2 is supplied by the mixture of 3076 g/h of residue from column C1 and 947 g/h of condensed distillate from column C3, whose composition is given in the fifth column of the table. The pressure is 5 bars, the reflux ratio 1.1 and the column is regulated to supply 307 g/h of distillate. The composition of the distillate produced, constituted by purified butenes, is given in the fourth column of the table.

Column C3 is supplied at the level of the eighth tray by the residue of column C2 and at a rate of 3716 g/h. It operates under atmospheric pressure with a reflux ratio of 1. The distillate is drawn off with a flow rate of 947 g/h and is recycled to the column C2, as described hereinbefore. The residue, constituted by quasi-pure DMF, is recycled to the column C1.

|  | Charge C1 | Distillate C1 | Distillate C2 | Distillate C3 |
|---|---|---|---|---|
| Flow rate g/h | 435 | 129 | 307 | 947 |
| Composition % by weight |  |  |  |  |
| isobutane | 18.4 | 62.2 | 0.02 | — |
| N-butane | 10.5 | 30.0 | 2.25 | — |
| 1-butene | 23.3 | 7.35 | 30.0 | — |
| isobutene | 1.5 | 0.38 | 2.03 | — |
| trans 2-butene | 27.9 | 0.06 | 39.6 | — |
| cis 2-butene | 18.4 | 0.01 | 26.1 | — |
| DMF | — | — | — | 4.36 |
| hexane | — | — | — | 95.64 |

The entire disclosure of all applications, patents and publications, cited above and below, and of French 91/03477, filed Mar. 20, 1991, are hereby incorporated by reference.

The preceding example can be repeated with similar success by substituting the generically or specifically described reactants and/or operating conditions of this invention for those used in the preceding example.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the separation of butanes and butenes from a charge containing the same, comprising:
   introducing said charge into an extractive distillation column under pressure;
   contacting said charge in said extractive distillation column with a first polar solvent S1, in which the butanes have a higher volatility than the butenes;
   withdrawing an overhead from the top of said extractive distillation column, said overhead consisting essentially of butanes;
   withdrawing residue from the bottom of said extractive distillation column, said residue comprised mainly of solvent S1 and butenes;
   providing a second solvent S2 having a volatility between that of the first solvent S1 and that of the butenes, which does not form an azeotrope with the butenes and which is miscible with said first solvent S1;
   passing said residue and said second solvent S2 into a desorption column under pressure;
   withdrawing from said desorption column an overhead consisting essentially of butenes;
   withdrawing a residue from said desorption column, said residue consisting essentially of a mixture of solvents S1 and S2;
   feeding said mixture into a purification column;
   withdrawing from said purification column an overhead consisting essentially of said solvent S2;
   condensing the latter overhead to form a distillate consisting essentially of said solvent S2;
   recycling the resultant distillate to the desorption column;
   withdrawing from the bottom of the purification column a bottom residue consisting essentially of purified solvent S1; and
   recycling said purified solvent to the extractive distillation column.

2. A process according to claim 1, wherein the first polar solvent S1 is monomethyl formamide, dimethyl formamide, diethyl formamide, dimethyl acetamide or N-methyl pyrrolidone.

3. A process according to claim 2, wherein the second solvent S2 has a boiling point of 30°–80° C.

4. A process according to claim 2, wherein the second solvent S2 is methyl tert. butyl ether or at least one $C_5$- or $C_6$-hydrocarbon.

5. A process according to claim 4, wherein the second polar solvent S2 is hexane, cyclohexane, or benzene.

6. A process according to claim 1, wherein the second solvent S2 has a boiling point of 30°–80° C.

7. A process according to claim 1, wherein the second solvent S2 is methyl tert. butyl ether, or at least one $C_5$- or $C_6$-hydrocarbon.

8. A process according to claim 7, wherein the second polar solvent S2 is hexane, cyclohexane, or benzene.

9. A process according to claim 1, wherein the extractive distillation column operates under a pressure of 4–10 bars, the solvent S1 being introduced into the upper part of the extractive distillation column at a flow rate in a weight ratio of 3 to 15 with the flow rate of said charge, the column bottom temperature being 90°–140° C. and the top temperature being 30°–70° C.

10. A process according to claim 9, wherein the solvent S2 is introduced into the desorption column at a flow rate of 15–50% compared with that of the solvent S1 introduced into the desorption column, the pressure of said desorption column being 4–10 bars, the bottom temperature is 150°–170° C., and the top temperature is 40°–60° C.

11. A process according to claim 10, wherein the first polar solvent S1 is monomethyl formamide, dimethyl formamide, diethyl formamide, dimethyl acetamide, or N-methyl pyrrolidone, and the second solvent S2 is methyl tert. butyl ether, or at least one $C_5$- or $C_6$-hydrocarbon.

12. A process according to claim 11, wherein the second polar solvent S2 is hexane, cyclohexane, or benzene.

13. A process according to claim 9, wherein the pressure of the purification column is approximately 1 bar, the bottom temperature is 140°–170° C. and the top temperature is 30°–100° C.

14. A process according to claim 13, wherein the first polar solvent S1 is monomethyl formamide, dimethyl formamide, diethyl formamide, dimethyl acetamide, or N-methyl pyrrolidone, and the second solvent S2 is methyl tert. butyl ether, or at least one $C_5$- or $C_6$-hydrocarbon.

15. A process according to claim 14, wherein the second polar solvent S2 is hexane, cyclohexane, or benzene.

16. A process according to claim 9, wherein the first polar solvent S1 is monomethyl formamide, dimethyl formamide, diethyl formamide, dimethyl acetamide, N-methyl pyrrolidone, and the second solvent S2 is methyl tert. butyl ether, or at least one $C_5$- or $C_6$-hydrocarbon.

17. A process according to claim 1, wherein the solvent S2 is introduced into the desorption column at a flow rate of 15–50% compared with that of the solvent S1 introduced into the desorption column, the pressure of said desorption column being 4–10 bars, the bottom temperature is 150°–170° C. and the top temperature is 40°–60° C.

18. A process according to claim 17, wherein the pressure of the purification column is approximately 1 bar, the bottom temperature is 140°–170° C. and the top temperature is 30°–100° C.

19. A process according to claim 18, wherein the first polar solvent S1 is monomethyl formamide, dimethyl formamide, diethyl formamide, dimethyl acetamide, or N-methyl pyrrolidone, and the second solvent S2 is methyl tert. butyl ether, or at least one $C_5$- or $C_6$-hydrocarbon.

20. A process according to claim 19, wherein the second polar solvent S2 is hexane, cyclohexane, or benzene.

21. A process according to claim 1, wherein the pressure of the purification column is approximately 1 bar, the bottom temperature is 140°–170° C. and the top temperature is 30°–100° C.

22. A process according to claim 1, wherein the butenes withdrawn as overhead from the desorption column are obtained with a purity of at least 97% by weight.

* * * * *